(12) United States Patent
Hamilton et al.

(10) Patent No.: US 8,494,611 B2
(45) Date of Patent: Jul. 23, 2013

(54) CARDIAC DIAGNOSTICS USING TIME COMPENSATED STRESS TEST CARDIAC MRI IMAGING AND SYSTEMS FOR CARDIAC DIAGNOSTICS

(75) Inventors: Craig A. Hamilton, Lewisville, NC (US); William Gregory Hundley, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 2560 days.

(21) Appl. No.: 10/629,259

(22) Filed: Jul. 29, 2003

(65) Prior Publication Data
US 2004/0024306 A1 Feb. 5, 2004

Related U.S. Application Data

(60) Provisional application No. 60/399,275, filed on Jul. 29, 2002, provisional application No. 60/421,704, filed on Oct. 28, 2002.

(51) Int. Cl.
*A61B 5/00* (2006.01)

(52) U.S. Cl.
USPC ............ 600/411; 600/407; 600/410; 600/508

(58) Field of Classification Search
USPC ... 600/410, 413, 440, 450, 428, 508; 382/131
See application file for complete search history.

(56) References Cited

U.S. PATENT DOCUMENTS

| | | | | |
|---|---|---|---|---|
| 5,111,820 A | | 5/1992 | Axel et al. | 128/653 |
| 5,377,680 A | * | 1/1995 | Bernstein et al. | 600/413 |
| 5,431,161 A | * | 7/1995 | Ryals et al. | 600/425 |
| 5,542,992 A | * | 8/1996 | Hashimoto et al. | 148/421 |
| 5,619,995 A | * | 4/1997 | Lobodzinski | 600/425 |
| 5,680,862 A | * | 10/1997 | Song et al. | 600/410 |
| 5,997,883 A | * | 12/1999 | Epstein et al. | 324/306 |
| 6,086,537 A | * | 7/2000 | Urbano et al. | 600/443 |
| 6,312,382 B1 | | 11/2001 | Mucci et al. | 600/437 |
| 6,500,123 B1 | * | 12/2002 | Holloway et al. | 600/443 |
| 6,558,324 B1 | * | 5/2003 | Von Behren et al. | 600/440 |
| 6,757,423 B1 | * | 6/2004 | Amini | 382/154 |

(Continued)

OTHER PUBLICATIONS

Bellenger et al. "Reduction in Sample Size for Studies of Remodeling in Heart Failure by the Use of Cardiovascular Magnetic Resonance" *J Cardiovascular Mangn Reson* 2(4): 271-278 (2000) (Abstract).

(Continued)

*Primary Examiner* — Unsu Jung
*Assistant Examiner* — Amanda Lauritzen
(74) *Attorney, Agent, or Firm* — Myers Bigel Sibley & Sajovec, PA (57) ABSTRACT

Methods of cardiac diagnostics of a patient are provided that include administering a stress test to the patient, acquiring a plurality of MRI cine loops of the heart of the patient at a plurality of heart rates, adjusting the plurality of MRI cine loops based on a heart rate associated with respective ones of the MRI cines so as to compensate for differences in heart rate and evaluating the compensated MRI cine loops so as to assess a state of coronary physiology of the patient. Furthermore, the administration of the stress test may be adjusted based on the evaluated compensated MRI cine loops. Also, the evaluation of the compensated MRI cine loops may determine a presence or absence of coronary artery disease based on the compensated cine loops.

33 Claims, 6 Drawing Sheets

U.S. PATENT DOCUMENTS

| | | | |
|---|---|---|---|
| 6,806,709 B2 * | 10/2004 | Markl et al. | 324/309 |
| 7,209,777 B2 * | 4/2007 | Saranathan et al. | 600/410 |
| 2002/0077538 A1 * | 6/2002 | Saranathan et al. | 600/410 |
| 2002/0087068 A1 * | 7/2002 | Foo | 600/413 |
| 2003/0161440 A1 * | 8/2003 | Boyd et al. | 378/98.12 |
| 2003/0206646 A1 * | 11/2003 | Brackett | 382/128 |
| 2004/0015079 A1 * | 1/2004 | Berger et al. | 600/437 |
| 2004/0073105 A1 * | 4/2004 | Hamilton et al. | 600/410 |
| 2006/0161060 A1 * | 7/2006 | Pai | 600/431 |

OTHER PUBLICATIONS

Bristow et al. "Doxorubicin Cardiomyopathy: Evaluation by Phonocardiography, Endomyocardial Biopsy, and Cardiac Catheterization" *Annals of Internal Medicine* 88: 168-175 (1978).

Cerqueira et al. "Standardized Myocardial Segmentation and Nomenclature for Tomographic Imaging of the Heart: A Statement for Healthcare Professionals from the Cardiac Imaging Committee of the Council on Clinical Cardiology of the American Heart Association" *Circulation* 150: 539-542 (2002).

Choi et al. "Transmural Extent of Acute Myocardial Infarction Predicts Long-Term Improvement in Contractile Function" *Circulation* 104: 1101-1107 (2001).

Chuang et al. "Importance of Imaging Method Over Imaging Modality in Noninvasive Determination of Left Ventricular Volumes and Ejection Fraction: Assessment by Two- and Three-Dimensional Echocardiography and Magnetic Resonance Imaging" *Journal of the American College of Cardiology* 35(2): 477-484 (2000).

Darty et al. "Nursing Responsibilities During Cardiac Magnetic Resonance Imaging" Department of Internal Medicine (Cardiology Section) and Radiology at the Wake Forest University School of Medicine (no date).

Del Carlo et al. "Cardiac Troponins in Congestive Heart Failure" *American Heart Journal* 138: 646-653 (1999).

Gerber et al. "Relation Between Gd-DTPA Contrast Enhancement and Regional Inotropic Response in the Periphery and Center of Myocardial Infarction" *Circulation* 104:998-1004 (2001).

Gianni et al. "Cardiac Function Following Combination Therapy with Taxol (T) and Doxorubicin (A) for Advanced Breast Cancer (ABC)" *Proceedings of ASCO* vol. 17 (1998) (Abstract).

Gottdiener et al. "Doxorubicin Cardiotoxicity: Assessment of Late Left Ventricular Dysfunction by Radionuclide Cineangiography" *Annals of Internal Medicine* 94(part 1): 430-435 (1981).

Hundley et al. "Relation of Cardiac Prognosis to Segment Location with Apical Left Ventricular Ischemia" *The American Journal of Cardiology* 92: 1206-1208 (2003).

Jacobson et al. "Magnetic Resonance Imaging of the Cardiovascular System: Present State of the Art and Future Potential" *JAMA* 259(2): 253-259 (1988).

Jensen et al. "Functional Monitoring of Anthracycline Cardiotoxicity: A Prospective, Blinded, Long-Term Observational Study of Outcome in 120 Patients" *Annals of Oncology* 13: 699-709 (2002).

Judd et al. "Physiological basis of Myocardial Contrast Enhancement in Fast Magnetic Resonance Images of 2-Day-Old Reperfused Canine Infarcts" *Circulation* 92: 1902-1910 (1995).

Kellman et al. "Phase-Sensitive Inversion Recover for Detecting Myocardial Infarction Using Gadolinium-Delayed Hyperenhancement" *Magnetic Resonance in Medicine* 47: 372-383 (2002).

Kim et al. "The Use of Contract-Enhanced Magnetic Resonance Imaging to Identify Reversible Myocardial Dysfunction" *New England Journal of Medicine* 343: 1445-1453 (2000).

Longmore et al. "Dimensional Accuracy of Magnetic Resonance in Studies of the Heart" *The Lancet* pp. 1360-1362 (Jun. 15, 1985).

Lorenz et al. "Normal Human Right and Left Ventricular Mass, Systolic Function, and Gender Differences by Cine Magnetic Resonance Imaging" *J Cardiovascular Magn Reson* 1(1): 7-21 (1999).

Maisel et al. "B-Type Natriuretic Peptide Levels: Diagnostic and Prognostic in Congestive Heart Failure: What's Next?" *Circulation* 150: 2328-2331 (2002).

Martin et al. "Imaging Cardiac Structure and Pump Function" *Cardiac Magnetic Resonance Imaging* 16(2): 135-160 (1998).

McDonagh et al. "Biochemical Detection of Left-Ventricular Systolic Dysfunction" *The Lancet* 351: 9-13 (1998).

Pattynama et al. "Left Ventricular Measurements with Cine and Spin-Echo MR Imaging: A Study of Reproducibility with Variance Component Analysis" *Radiology* 187: 261-268 (1993).

Rector et al. "Assessment of Patient Outcome with the Minnesota Living Heart Failure Questionnaire: Reliability and Validity During Randomized, Double-Blind, Placebo-Controlled Trial of Pimobendan" *American Heart Journal* 124: 1017-1025 (1992).

Rehr et al. "Left Ventricular Volumes Measured by MR Imaging" *Radiology* 156: 717-719 (1985).

Rerkpattanapipat et al. "Clinical Utility of Assessments of Left Ventricular Systolic Function and Coronary Arterial Blood Flow During Pharmacological Stress with Magnetic Resonance Imaging" *Topics in Magnetic Resonance Imaging* 11(6): 399-405 (2000).

Schwartz et al. "Congestive Heart Failure and Left Ventricular Dysfunction Complicating Doxorubicin Therapy" *The American Journal of Medicine* 82: 1109-1118 (1987).

Sechetem et al. "Measurement of Right and Left Ventricular Volumes in healthy Individuals with cine MR Imaging" *Radiology* 163: 697-702 (1987).

Semelka et al. "Interstudy Reproducibility of Dimensional and Functional Measurements Between Cine Magnetic Resonance Studies in the Morphologically Abnormal Left Ventricle" *American Heart Journal* 119: 1367-1373 (1990).

Stratemeier et al. "Ejection Fraction Determination by MR Imaging: Comparison with Left Ventricular Angiography" *Radiology* 158: 775-777 (1986).

Wu et al. "Visualisation of Presence, Location, and Transmural Extent of Healed Q-Wave and Non-Q-Wave Myocardial Infarction" *The Lancet* 357: 21-28 (2001).

International Search Report dated Jan. 13, 2004 for corresponding PCT application No. PCT/US03/23668.

Hundley et al. "Utility of Fast Cine Magnetic Resonance Imaging an display for the Detection of Myocardial Ischemia in patients Not Well Suited for Second Harmonic Stress Echocardiography" *Circulation* 100: 1697-1702 (1999).

Hamilton et al. "Is Imaging at Intermediate Doses Necessary During Dobutamine Stress Magnetic Resonance Imaging?" *Journal of Cardiovascular Magnetic Resonance* 3(4): 297-302 (2001).

International Search Report dated Jan. 23, 2004 for related PCT application No. PCT/US03/23526.

Sechtem et al., "Quantification of Cardiac Function by Conventional and Cine Magnetic Resonance Imaging", CardioVascular and Interventional Radiology, (1987) 10:365-373.

American Heart Association (AHA) 1999—Poster Presentation with Abstract, 2 sheets.

Hamilton et al. "Near-real-time Cardiac Cine-MR Monitoring during High-dose Pharmacologic Stress Testing", Radiology (suppl) 1998; 209(P):229.

Hamilton et al., "Near-real-time Cine-MR Monitoring in High-dose Dobutamine Cardiac Stress Testing," RSNA PowerPoint Presentation, 20 pages (1998).

* cited by examiner

CARDIAC DIAGNOSTICS USING TIME COMPENSATED STRESS TEST CARDIAC MRI IMAGING AND SYSTEMS FOR CARDIAC DIAGNOSTICS

RELATED APPLICATIONS

This application claims the benefit of priority of U.S. Provisional Patent Application Ser. No. 60/399,275, filed Jul. 29, 2002, and U.S. Provisional Patent Application Ser. No. 60/421,704 filed Oct. 28, 2002, the contents of which are hereby incorporated by reference as if recited in full herein.

FIELD OF THE INVENTION

The present invention is related to cardiac diagnostics and more particularly to stress test cardiac diagnostics using magnetic resonance imaging (MRI) methods.

BACKGROUND OF THE INVENTION

The heart is a muscle that continuously pumps blood, transporting life sustaining oxygen and nutrients to the major organs and tissues of the body. As such, the heart needs a large supply of oxygen and nutrients. The heart receives its blood from three major coronary arteries. If any one of these arteries becomes narrowed or blocked, blood flow and oxygen to the heart is restricted, the performance of your blood pump is impaired, and permanent damage to the heart can occur. An impaired or damaged heart can significantly impact quality of life and even result in death.

Coronary artery disease (CAD) is the primary cause of narrowing and blockage of the arteries to or in the heart. It is the leading cause of death in the United States. Although the rate of death due to CAD has declined steadily over the last few decades, the overall incidence of CAD and the impact it will have on the population and the cost of health care is expected to grow dramatically over the next 20-30 years due to the aging population. CAD already costs the U.S. an estimated $100 billion annually in medical care and lost productivity. Therefore, the tests for CAD that can improve the accuracy of cardiac evaluations, particularly in early stage coronary heart disease/CAD, may be beneficial. Tests that may allow physicians to make explicit diagnoses and treatment plans, that may reduce unnecessary tests, surgeries and hospital stays, may reduce anxiety, discomfort and risk to the patient and/or may allow for the assessment of therapeutic efficacy may be particularly beneficial.

The ability to mitigate and circumvent the effects of CAD has improved over the years as a result of the prior development of increasingly sophisticated cardiac tests and procedures. The "gold standard" of cardiac tests is generally recognized as cardiac catheterization and angiography. This test is most commonly used in determining the location and the severity of the effects of CAD. However, a cardiac catheterization procedure is an expensive procedure that typically requires hospitalization because it is invasive and has potential for complications. As a result, cardiac catheterization procedures are generally only used when a patient has undergone other non-invasive tests such as cardiac stress tests with significant abnormal results. More than one million cardiac catheterization procedures are performed each year at a cost estimated to be between about $3-$5 billion.

Cardiac stress tests may be particularly important in evaluating the heart and its coronary arteries because often the presence of CAD and its effects are missed when tests are performed on a patient at rest. It is only when the heart is stressed by either exercise on a treadmill or exercise bike, or where the maximal exercise is simulated by the introduction of special chemicals or drugs (drug-induced stress) to the heart of patients who for various reasons are unable to perform actual physical exercise, that the symptoms of CAD can be reliably detected over much of the population. Currently, the most commonly used stress tests include the exercise (treadmill) stress test, the stress echocardiogram (ultrasound), and the nuclear perfusion stress test.

These three tests have varying levels of complexity, accuracy, availability, and cost. The ECG exercise stress test is the most widely available and used stress test and the least costly to administer. It relies on detection of changes in ST segments on a 12-lead echocardiogram; it is variable in its accuracy, producing a significant number of false positive and negative results. Consequently, patients often undergo supplemental imaging during their stress test with echocardiography or radionuclide scintigraphy. The sophistication of both echocardiography and radionuclide scintigraphy stress tests typically require that they be administered and evaluated by a specialist. Typically, a trained ultrasound technician or a cardiologist administers a stress echocardiogram, and a technician certified in the handling of radioisotopes along with a cardiologist or radiologist administers a nuclear perfusion stress test. Results in both testing protocols generally need to be evaluated by a cardiologist in order to make an accurate diagnosis. The test selected for administration is typically determined by the cardiologist based on the findings of the physical and medical history of the patient and the cardiologist's clinical judgment. Each test has a degree of inaccuracy. The echocardiography has an almost 10-15% failure rate where a diagnosis cannot be made. Obstacles that may prevent the capture of good images for diagnosis may cause this failure rate. Scar tissue from chest surgeries, excessive patient body fat and lung disorders that capture excessive oxygen in the lungs are examples of such obstacles. Stress echocardiography tests, for varying reasons, also produce a significant number of false negative results. The nuclear perfusion stress tests are highly sensitive and are prone to produce an equally significant number of false positive results.

With over 1.3 million stress echocardiography tests performed each year with a 10-15% failure rate, there are potentially over $100 million unnecessary or clinically unreliable stress echocardiography tests done each year. This stress echo failure rate results in an increase in the number of nuclear perfusion stress tests, which are known to have a high incidence of false positive results. A false positive cardiac stress test may increase the number of expensive, unnecessary cardiac catheterization procedures and their associated required hospital stay and added anxiety, discomfort and medical risk for the patient. The significant number of false negatives from stress echocardiography tests may increase the risk of heart attacks and sudden death from undetected advanced CAD and/or successful earlier intervention in early stages of CAD.

Accordingly, a need exists for reduced cost, increased accuracy and/or increased availability stress testing for cardiac diagnostics.

SUMMARY OF THE INVENTION

Embodiments of the present invention provide methods of cardiac diagnostics of a patient that include administering a stress test to the patient, acquiring a plurality of MRI cine loops of the heart of the patient at a plurality of heart rates and levels of pharmacologic or exercise induced stress, adjusting the plurality of MRI cine loops based on a heart rate associated with respective ones of the MRI cines so as to compensate for differences in heart rate and evaluating the compensated MRI cine loops so as to assess a state of coronary physiology of the patient. Furthermore, the administration of the stress test may be adjusted based on the evaluated compensated MRI cine loops. Also, the evaluation of the compensated MRI cine loops may determine a presence or absence of myocardial ischemia or viability based on the displayed cine loops.

In further embodiments of the present invention, a plurality of the compensated MRI cine loops are simultaneously displayed. For example, a plurality of cine loops for differing locations associated with the heart of the patient for a single dosage of a stress inducing agent or level of exercise. A plurality of cine loops for a single location associated with the heart of the patient for differing dosages of a stress inducing agent could also be displayed.

In still other embodiments of the present invention, the plurality of MRI cine loops are adjusted by adding frames to and/or removing frames from at least one of the plurality of MRI cine loops. Frames may be added to and/or removed from respective ones of the MRI cine loops such that all of the MRI cine loops have a same number of frames. Frames may be added by repeating frames of an MRI cine loop. Also, the frames that are added or removed may be evenly distributed throughout an MRI cine loop. In particular embodiments, the MRI cine loops are compensated such that corresponding frames in each of the plurality of MRI cine loops correspond to a common relative time within a cardiac cycle of the patient.

In additional embodiments of the present invention, the plurality of MRI cine loops are adjusted by adjusting a duration of display of frames of a least one of the plurality of MRI cine loops such that each of the MRI cine loops has a common total duration. The frames for which the duration is adjusted may be evenly distributed throughout the MRI cine loop.

In further embodiments of the present invention, evaluating the compensated MRI cine loops is provided by comparing at least two of the plurality of cine loops to each other. Furthermore, one of the two of the plurality of cine loops may be a baseline MRI cine loop. Frames of the plurality of MRI cine loops may be registered to the baseline MRI cine loop.

In other embodiments of the present invention, MRI cine loops are displayed by adjusting a characteristic of one frame of a plurality of frames of an MRI cine loop and propagating the adjustment of the one frame to other frames of the MRI cine loop. Furthermore, where a plurality of other MRI cine loops are displayed, the adjustment of the one frame to may be propagated to frames of the other MRI cine loops.

Additionally, the adjustment may be cropping a frame of the plurality of frames to provide a portion of the frame. The adjustment could also be adjusting a display level of the frame.

As will be appreciated by those of skill in the art in light of the present disclosure, embodiments of the present invention may be provided as methods, systems and/or computer program products.

DESCRIPTION OF EMBODIMENTS OF THE INVENTION

The present invention now will be described more fully hereinafter with reference to the accompanying drawings, in which illustrative embodiments of the invention are shown. This invention, however, should not be construed as limited to the embodiments set forth herein; rather, these embodiments are provided so that this disclosure will be thorough and complete, and will fully convey the scope of the invention to those skilled in the art.

As will be appreciated by one of skill in the art, the present invention may be embodied as methods, systems, or computer program products. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. Particular cine display systems may utilized Interactive Data Language (IDL) of Research Systems, Inc., Boulder, Colo., to provide cine displays suitable for use in embodiments of the present invention. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). Furthermore, the user's computer, the remote computer, or both, may be integrated into other systems, such as an MRI system.

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Embodiments of the present invention provide for the cardiac diagnostics utilizing temporally synchronized MRI cines of the heartbeat of a patient. The temporally synchronized MRI cines are adjusted to compensate for different heart rates and, accordingly, different cardiac cycle durations. Cardiac diagnostics is performed by evaluating the temporally synchronized MRI cines of a patient being subjected to stress testing. Such evaluation may result in a screening determination as to whether or not a patient likely has CAD.

Figure 1:
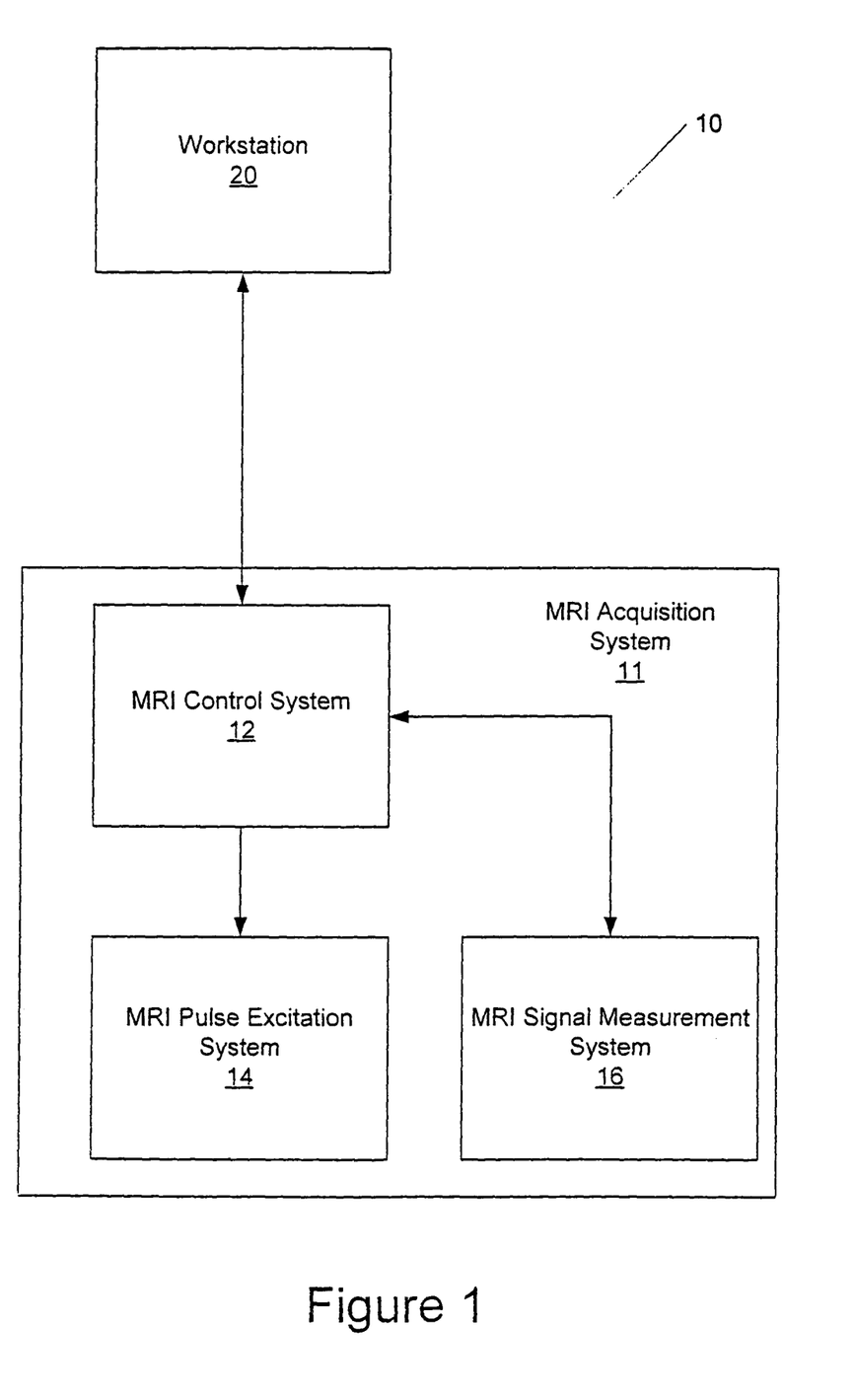
FIG. 1 is a block diagram of an MRI system suitable for use according to embodiments of the present invention.

An exemplary system 10 according to embodiments of the present invention is illustrated in FIG. 1. As seen in FIG. 1, a cine display/MRI system 10 includes an MRI acquisition system 11 that may include an MRI control system circuit 12, an MRI pulse excitation system circuit 14 and an MRI signal measurement system circuit 16. The MRI control system circuit 12 controls operations of the MRI acquisition system 11 to obtain and provide MRI images during a cardiac cycle of a patient. The MRI control system circuit 12 may also assemble and transmit the acquired images to a workstation 20 or other such data processing system for further analysis and/or display. The workstation 20 may be in an MRI suite or may be remote from the MRI suite. The MRI pulse excitation system circuit 14 and the MRI signal measurement system circuit 16 are controlled to acquire MRI signals that may provide MRI images of the heart of a patient.

The MRI images may be acquired, for example, utilizing a fast gradient echo segmented k-space sequence. The k-space segmentation may be adjusted to provide adequate temporal resolution (13-65 msec) for identification of end of systole, with the end-systolic frame typically being the frame with the smallest left ventricle (LV) cavity dimensions. View sharing may be utilized to provide an intermediate frame between acquired frames. The table below provides an example of the adjustment of k-space segmentation for differing heart rates.

| Heart Rate (beats/min) | Views per Segment | Temporal Resolution (msec) | Breathhold Duration (sec) |
| --- | --- | --- | --- |
| <55 | 10 | 65 | 10 |
| 55-65 | 8 | 52 | 13-11 |
| 65-95 | 6 | 39 | 15-10 |
| 95-125 | 4 | 26 | 15-12 |
| 125-170 | 2 | 13 | 23-17 |

Alternatively, images may be acquired with other MRI techniques highlighting thickening or relaxation of the LV myocardium.

The MRI images of the frames of the cine loops may include corresponding images of different locations of the heart and at different times during the cardiac cycle of the patient. For example, the images may include slices such as the basal short axis, the long axis, the mid short axis, the apical short axis, four chamber and two chamber slices. In particular embodiments, the desired locations may be selected so as to provide images of LV wall motion. Furthermore, the images may be from different times during a stress test of the patient, for example, at a baseline or resting heart rate and/or at different heart rates and/or different dosages of stress inducing agents, such as dobutamine and atropine or different levels of exercise.

Conventional MRI systems, such as those provided by General Electric Medical Systems, Siemens, Philips, Varian, Bruker, Marconi and Toshiba may be utilized to provide the desired MRI image frames collected during heartbeats of a patient undergoing stress testing that may be temporally compensated and displayed and/or analyzed for biophysical or biophysiological abnormalities for cardiac diagnostics according to embodiments of the present invention as described herein.

While an exemplary cine display/MRI system is illustrated in FIG. 1 and described herein with a particular division of functions and/or operations, as will be appreciated by those of skill in the art, other divisions of functions and/or operations may be utilized while still benefiting from the teachings of the present invention. For example, the MRI control system circuit 12 could be combined with either the MRI pulse excitation system circuit 14 or the MRI signal measurement system circuit 16. Thus, the present invention should not be construed as limited to a particular architecture or division of MRI functions/operations but is intended to cover any architecture or division of functions/operations capable of carrying out the operations described herein.

Figure 2:
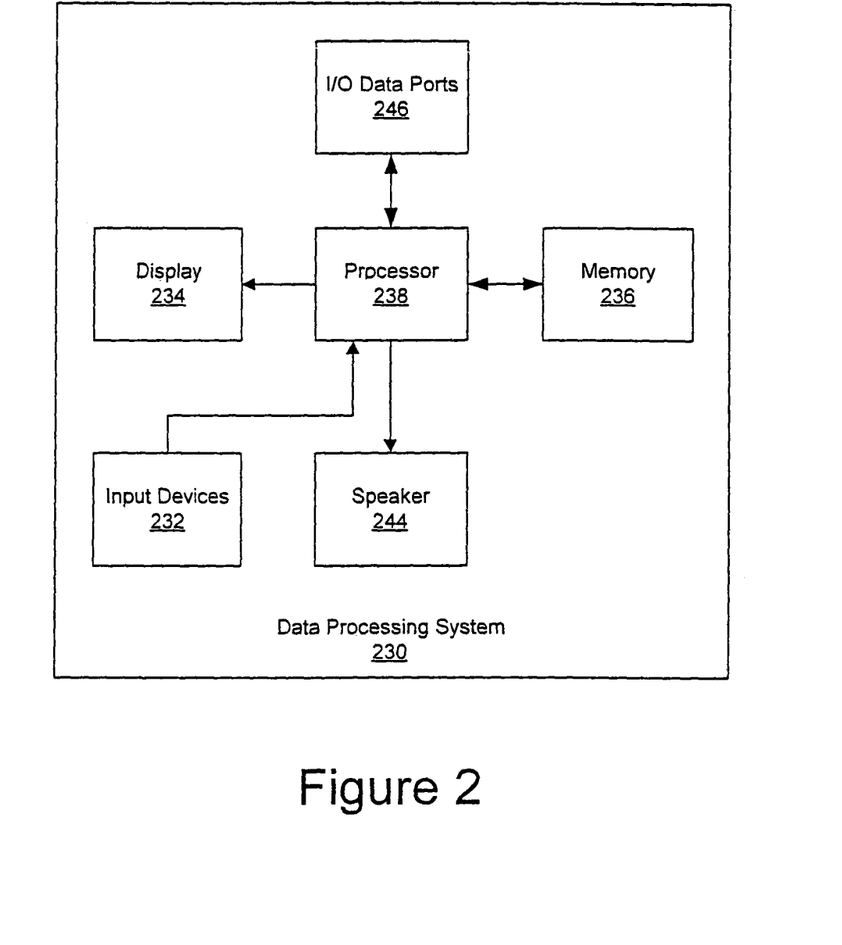
FIG. 2 is a block diagram of a data processing system suitable for use according to embodiments of the present invention.

FIG. 2 illustrates an exemplary embodiment of a data processing system 230 suitable for providing a workstation 20 and/or MRI control system circuit 12 in accordance with embodiments of the present invention. The data processing system 230 typically includes input device(s) 232 such as a keyboard or keypad, a display 234, and a memory 236 that communicate with a processor 238. The data processing system 230 may further include a speaker 244, and an I/O data port(s) 246 that also communicate with the processor 238. The I/O data ports 246 can be used to transfer information between the data processing system 230 and another computer system or a network. These components may be conventional components such as those used in many conventional data processing systems that may be configured to operate as described herein.

Figure 3:
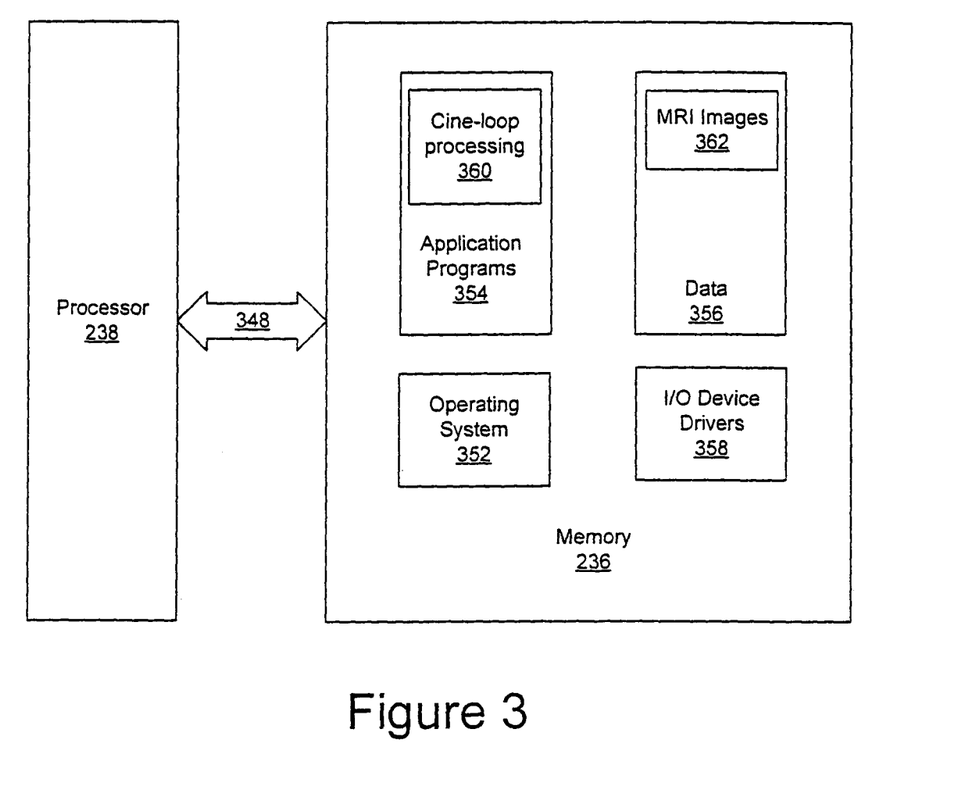
FIG. 3 is a more detailed block diagram of a data processing system suitable for use according to embodiments of the present invention.

FIG. 3 is a block diagram of embodiments of data processing systems that illustrates systems, methods, and computer program products in accordance with embodiments of the present invention. The processor 238 communicates with the memory 236 via an address/data bus 348. The processor 238 can be any commercially available or custom microprocessor. The memory 236 is representative of the overall hierarchy of memory devices containing the software and data used to implement the functionality of the data processing system 230. The memory 236 can include, but is not limited to, the following types of devices: cache, ROM, PROM, EPROM, EEPROM, flash memory, SRAM, and DRAM.

As shown in FIG. 3, the memory 236 may include several categories of software and/or data used in the data processing system 230: the operating system 352; the application programs 354; the input/output (I/O) device drivers 358; and the data 356. As will be appreciated by those of skill in the art, the operating system 352 may be any operating system suitable for use with a data processing system, such as OS/2, AIX or System390 from International Business Machines Corporation, Armonk, N.Y., Windows95, Windows98, Windows2000, WindowsNT or WindowsXP from Microsoft Corporation, Redmond, Wash., Unix or Linux. The operating systems may be configured to support an TCP/IP-based or other such network communication protocol connection. The I/O device drivers 358 typically include software routines accessed through the operating system 352 by the application programs 354 to communicate with devices such as the I/O data port(s) 246 and certain memory 236 components. The application programs 354 are illustrative of the programs that implement the various features of the data processing system 230 and preferably include at least one application that supports operations according to embodiments of the present invention. Finally, the data 356 represents the static and dynamic data used by the application programs 354, the operating system 352, the I/O device drivers 358, and other software programs that may reside in the memory 236.

As is further seen in FIG. 3, the application programs 354 may include a cine-loop processing application 360. The cine-loop processing application 360 may carry out the operations described herein for temporally synchronizing cine loops of MRI images, displaying temporally synchronized cine loops of MRI images and/or evaluation of temporally synchronized cine loops of MRI images. The data portion 356 of memory 236, as shown in the embodiments of FIG. 3, may include MRI image data 362 that includes cine loops of MRI images.

While the present invention is illustrated, for example, with reference to the cine-loop processing application 360 being an application program in FIG. 3, as will be appreciated by those of skill in the art, other configurations may also be utilized while still benefiting from the teachings of the present invention. For example, the cine-loop processing application 360 may also be incorporated into the operating system 352, the I/O device drivers 358 or other such logical division of the data processing system 230. Thus, the present invention should not be construed as limited to the configuration of FIG. 3 but is intended to encompass any configuration capable of carrying out the operations described herein.

Figure 4:
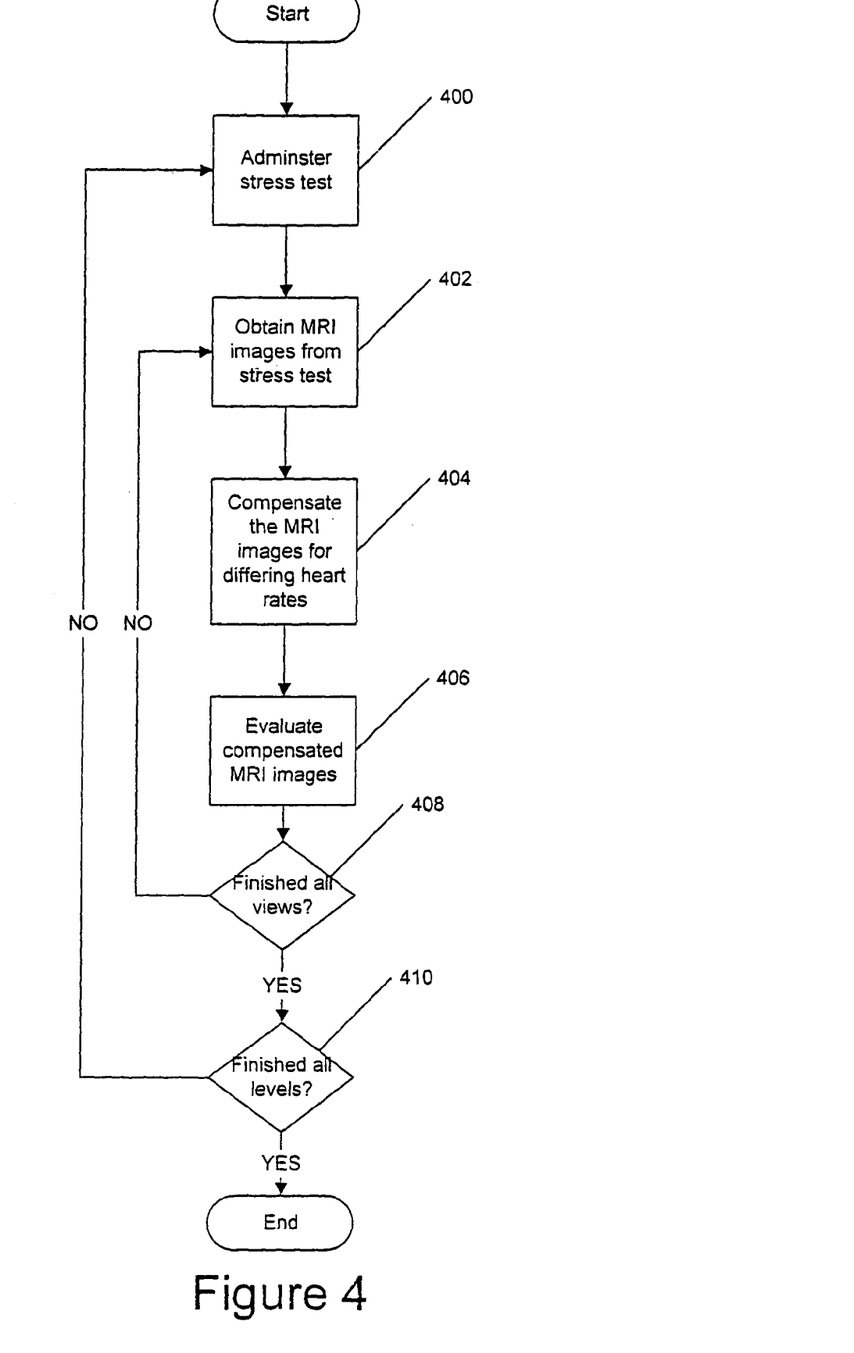
FIG. 4 is a flowchart illustrating operations according to embodiments of the present invention.

FIG. 4 illustrates operations according to certain embodiments of the present invention. As illustrated in FIG. 4, a stress test is administered to a patient (block 400) and MRI images of the heart of the patient are acquired during the stress test (block 402). The stress test may be any type of stress test that may be administered while MRI images are acquired. In particular embodiments the MRI stress test is a biochemically induced stress test using an agent such as dobutamine or the like or before, during or after exercise. The administration of cardiac stress tests are known to those of skill in the art and, therefore, are not described further herein.

The MRI images, which may provide cine loops of heart beats at differing locations of the heart and/or different dose levels of a stress inducing agent, are temporally synchronized such that each cine loop has the same number of MRI images or frames so as to compensate for different heart rates of the differing cine loops (block 404). Thus the absolute time corresponding to a given frame of a cine loop may differ between cine loops, however, the frames of different cine loops would correspond to approximately the same percentage of time of the cardiac cycle. The cine loops may also be synchronized to the cardiac cycle such that each cine loop begins at the same portion of the cardiac cycle. The compensated cine loops are then evaluated to asses a state of cardiac physiology of the patient (block 406), for example, by providing the cine loops to a workstation for display such that the evaluation occurs in near real time. Such an assessment may be made, for example, by displaying the cine loops for a given location for several or all doses and/or displaying the cine loops for several or all locations for a given dose. The displayed cine loops may be evaluated by a physician to assess cardiac physiology. Such an assessment may include, for example, a determination of the presence or absence of CAD, a change in the severity of CAD, the efficacy of a cardiac treatment regime or the like.

These operations may be repeated until the MRI images for the desired locations (block 408) and for the desired stress test levels (block 410) are obtained and compensated as described herein. Thus, if additional views are to be acquired (block 408) operations continue with obtaining additional MRI images (block 402). If additional stress levels are to be evaluated (block 410), operations continue with the administration of additional stress tests (block 400).

The temporal synchronization of the cine loops has been found to allow physicians to evaluate cardiac physiology more effectively without introducing artifacts and/or distortions through the temporal synchronization process that would obscure information or provide false information that would lead to invalid evaluations. Furthermore, the temporal synchronization of the cine loops has been found to increase the effectiveness of the evaluation of MRI cine loops as it allows the physician to simultaneously visually compare heart motion at different heart rates where the display heart motion is synchronized to the portion within the cardiac cycle. Thus, each displayed image is at approximately the same time within a heart beat. Accordingly, differences in wall motion at different heart rates may be directly compared to detect any abnormality. As discussed above, it has been found that the temporal synchronization process described herein allows for such a display without introducing inaccuracies, artifacts or other such distortions that would hinder the evaluation process. Furthermore, the evaluation process may be performed in a sufficiently real-time manner so as to allow a physician to utilize the MRI cine loops to monitor a stress test while the stress test is being performed. Such monitoring may be useful both in administering the stress test and in evaluation of a patient's condition based on the results of the stress test. By providing the cine loop information in a form that allows for simultaneous direct comparison of data for differing heart rates a physician may rapidly assess the cardiac physiology of a patient so as to adjust parameters of the test and/or avoid injury to the patient.

In still further embodiments of the present invention, the evaluation of the cine loops may be performed automatically or partially automatically utilizing image processing techniques. Such an automatic evaluation may be facilitated by the temporal synchronization of the cine loops as data sets having a common size would be provided and corresponding frames within the data sets would correspond to a common portion within a cardiac cycle. For example, the cine loops or a portion of the images within the cine loops may be compared to each other or a reference so as to highlight deviations from a baseline cine loop. Thus, for example, a baseline wall motion cine loop may be compared to differing dose cine loops and the differences displayed and/or compared to thresholds so as to provide an indication and/or assessment of cardiac physiology. Such a comparison of the cine loops may be made possible and/or simplified because the location within each cine loop corresponds to approximately the same time within the cardiac cycle such that similarly situated frames within differing cine loops may be directly compared to each other.

An automatic comparison may, for example, also include registration of the differing cine loops to the baseline loops. Such a registration may be provided utilizing conventional pattern recognition and/or alignment techniques such that corresponding pixels of the cine loops or portions of the cine loops are each associated with approximately the same physical location within the patient. In particular embodiments, the comparisons may be 3 (x,y, t), 4 (x,y,z,t) and/or 5 (x,y,z,t, dose) dimensional.

The cine loops may be compensated by repeating images, increasing or decreasing the time an image is displayed and/or by removing images from the cine loops. The cine loops may be temporally synchronized by providing the same number of images or frames in each loop. Thus, each displayed heartbeat of the patient may be displayed for the same period of time irrespective of the heart rate at which the cine loop was acquired. Loops which have more frames may have frames removed and loops with fewer frames may have frames added. Frames may be added by repeating frames in the loop. Frames may be added in a virtual manner by increasing the duration that a frame is displayed. Such a virtual addition of frame may need less storage requirement than the physical repetition of frames in a loop. The frames added or removed may be distributed throughout the loop and are preferably distributed substantially evenly throughout the loop. Furthermore, the cine loops may be synchronized to the patients cardiac cycle such that each cine loop begins at approximately the same part in the cardiac cycle. Techniques for synchronizing MRI cine loops to the cardiac cycle of a patient are known to those of skill in the art and, therefore, need not be described further herein.

In particular embodiments of the present invention, the display of cine loops is provided in real time. In other embodiments, the display of cine loops is provided in near real time. Such real time or near real time display of cine loops of a patient undergoing stress testing may be utilized to provide safe stress testing by allowing for rapid analysis and monitoring of the stress test such that patient injury may be avoided. In still other embodiments, the display of cine loops is provided from stored information and may be performed "off-line." Such off-line analysis may be suitable for detailed or more time consuming analysis of the cine loops. Furthermore, the acquisition of data, construction of images and/or the transfer of images of a cine loop may be overlapped with each other so as to reduce apparent latency between the acquisition and the display of images.

Figure 5:
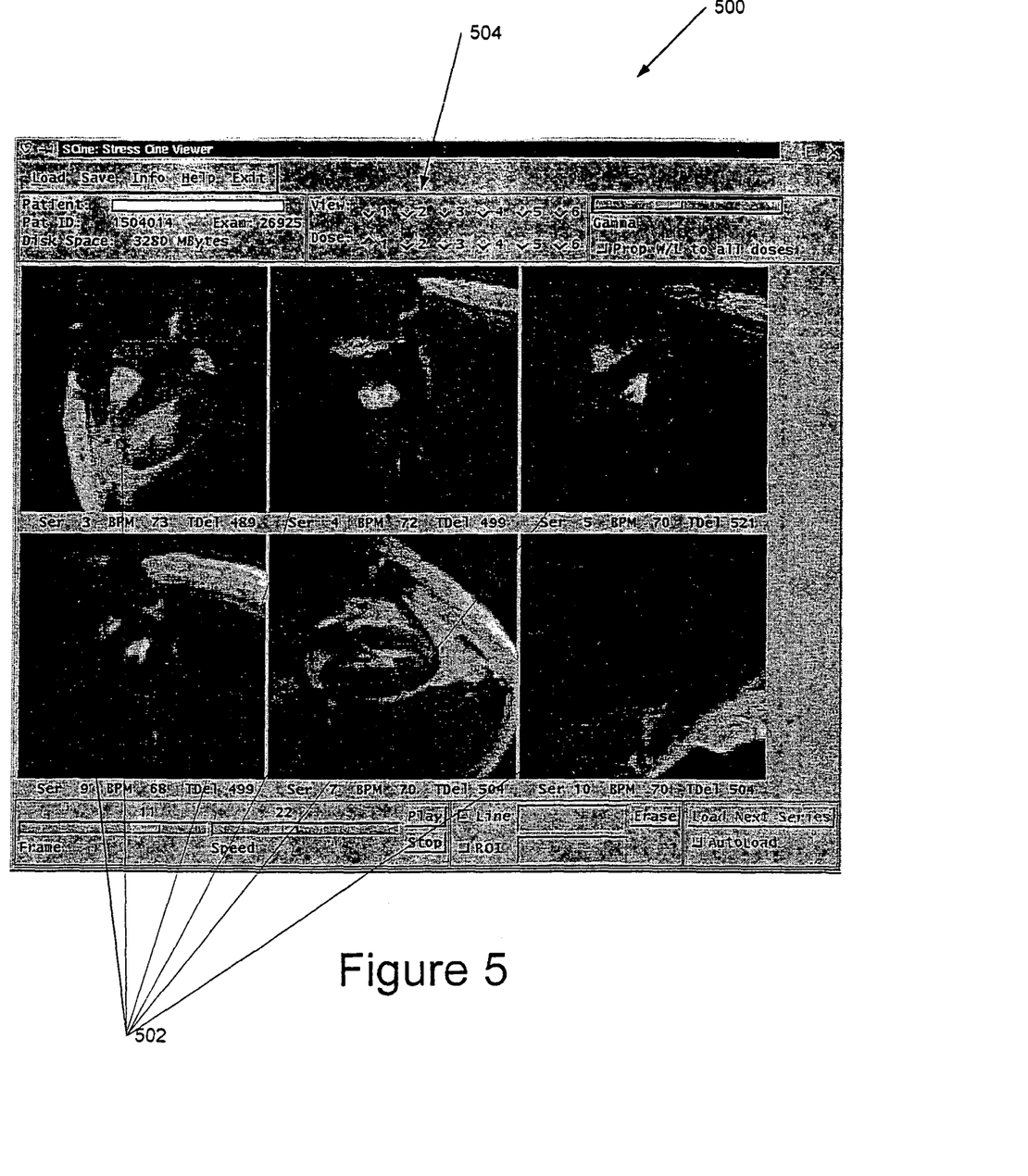
FIG. 5 is a screen capture of an exemplary cine-loop display.

FIG. 5 is a screen capture of a cine loop display 500 suitable for use in embodiments of the present invention. As seen in FIG. 5, a plurality of cine loops 502 are simultaneously displayed. The cine loops have been time synchronized as described above. As is seen in FIG. 5, the different cine loops have associated with them different heart rates, however, each cine loop is displayed for the same duration. FIG. 5 illustrates the display of different locations for the same dose, however, different doses may be selected and/or the display of the same location for different doses through the use of the radio buttons 504. Thus, a physician may rapidly switch between the various display mechanisms when evaluating the compensated cine loops.

Figure 6:
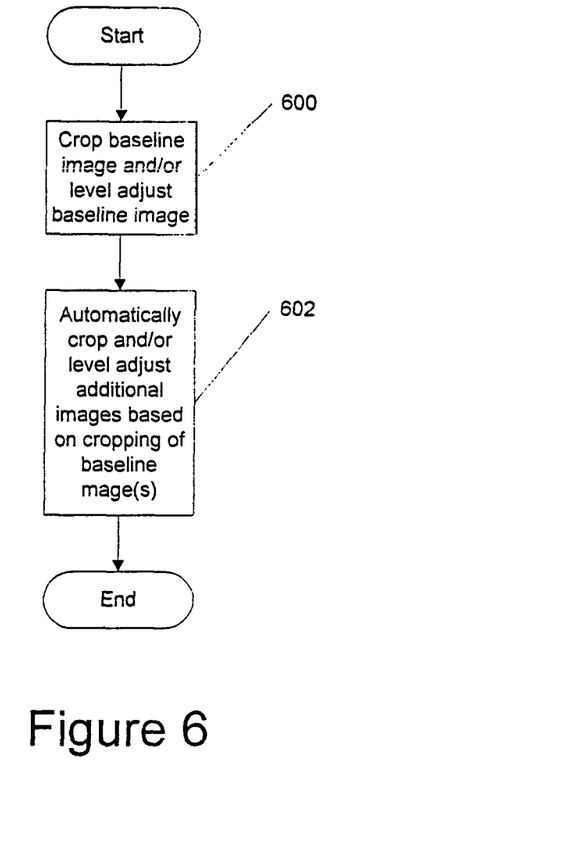
FIG. 6 is a flowchart illustrating operations according to further embodiments of the present invention.

FIG. 6 illustrates operations according to further embodiments of the present invention. As seen in FIG. 6, user input may be obtained to crop a cine loop base image and/or to adjust contrast, brightness, gamma or other display levels of the base cine loop image (block 600). The cropping and/or level adjustment may then be propagated automatically to the remaining images in the base cine loop and to the other cine loops that are displayed or are stored (block 604). Thus, a physician may rapidly adjust the display of the cine loop images without the need to adjust each image and/or loop individually. Optionally, the cropping and/or level information may be stored and associated with the cine loops. The cine loops may also be stored, for example, on a hard drive or other storage media, and recalled at a later time for display and/or analysis. The stored cine loops could then be displayed with the cropping and/or level information automatically applied.

While embodiments of the present invention have been described primarily with reference to near real time evaluation of the MRI images, as will be appreciated by those of skill in the art in light of the present disclosure, evaluation of the MRI images could also occur "off line" or after a substantial delay. For example, prior MRI images could be displayed and compared with current MRI images to determine if improvement, possibly resulting from a course of treatment, has occurred in wall motion and/or perfusion. Thus, the present invention should not be construed as limited to the evaluation of MRI cine loop images immediately after acquisition.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims.

That which is claimed is:

1. A method of cardiac diagnostics of a patient, comprising:

administering a stress test to the patient;

acquiring a plurality of different views of MRI cine-loops of the heart of the patient at a plurality of heart rates the different views comprising some views associated with a first anatomical view at different heart rates induced by different doses of a stress-inducing substance and some views associated with different anatomical views at a substantially constant heart rate, wherein the MRI cine-loops are generated using multiple MRI images that highlight thickening of the myocardia and form the frames of the cine loops;

temporally synchronizing the plurality of MRI cine loops with a processor;

adjusting, with the processor, the plurality of temporally synchronized MRI cine loops based on a heart rate associated with respective ones of the MRI cines so as to compensate for differences in heart rate so that each MRI cine loop has the same duration;

displaying a plurality of the adjusted MRI cine loops at a clinician workstation in substantially real-time while the patient is in an MRI scanner used for the acquiring step;

allowing a clinician to electronically select at least one of the following on the clinician workstation: (a) at least one dose amount, (b) at least one view, and (c) at least one dose amount and at least one view to define the MRI cine loops for the displaying step; and evaluating the compensated MRI cine loops with the processor so as to assess a state of coronary physiology of the patient, wherein the cine loops are displayed during the stress test to allow a physician to assess cardiac physiology of a patent so as to adjust parameters of the test and/or avoid injury to the patient thereby providing safer cardiac stress testing.

2. The method of claim 1, further comprising adjusting the administration of the stress test based on the evaluated compensated MRI cine loops.

3. The method of claim 1, wherein the evaluation of the compensated MRI cine loops comprises determining a presence or absence of coronary artery disease based on the compensated MRI cine loops.

4. The method of claim 1, wherein the allowing a clinician to electronically select step comprises providing electronic user inputs displayed apart from the display images of the MRI cine loops that are associated with selectable views and doses of the MRI cine loops that allow a user to select both at least one view and at least one dose amount for the MRI cine loops for the displaying step.

5. A method according to claim 1, wherein the step of allowing the clinician to electronically select at least one of the following: (a) at least one dose amount; (b) at least one view; or (c) at least one dose amount and at least one view to define the MRI cine loops for the displaying step allows the clinician to select each of (a), (b) and (c), and wherein the step of allowing the clinician to select is carried out to allow the clinician to rapidly switch between various display mechanisms.

6. The method of claim 1, further comprising simultaneously displaying a plurality of the compensated MRI cine loops.

7. The method of claim 6, wherein at least one of the plurality of compensated MRI cine loops comprises a resting heart rate cine loop.

8. The method of claim 6, wherein evaluation of the compensated MRI cine loops comprises determining a presence or absence of coronary artery disease based on the simultaneously displayed plurality of compensated MRI cine loops.

9. The method of claim 6, wherein simultaneously displaying a plurality of the compensated MRI cine loops comprises simultaneously displaying a plurality of cine loops for differing locations associated with the heart of the patient for a single dosage of a stress inducing agent.

10. The method of claim 6, wherein simultaneously displaying a plurality of the compensated MRI cine loops comprises simultaneously displaying a plurality of cine loops for a single location associated with the heart of the patient for levels of stress of the patient.

11. The method of claim 1, wherein adjusting the plurality of MRI cine loops comprises adding frames to at least one of the plurality of MRI cine loops.

12. The method of claim 1, wherein the adjusting comprises adding and/or removing frames from respective ones of the MRI cine loops such that all of the MRI cine loops have a same number of frames.

13. The method of claim 12, wherein the adding and/or removing frames comprises adding frames by repeating frames of an MRI cine loop.

14. The method of claim 12, wherein the frames that are added and/or removed are evenly distributed throughout an MRI cine loop.

15. The method of claim 1, wherein the MRI cine loops are compensated such that corresponding frames in each of the plurality of MRI cine loops correspond to a common relative time within a cardiac cycle of the patient.

16. The method of claim 1, wherein the MRI cine loops are compensated so that differing heart rates of the patient visually appear to have a same duration.

17. The method of claim 1, wherein adjusting the plurality of MRI cine loops comprises adjusting a duration of display of frames of a least one of the plurality of MRI cine loops such that each of the MRI cine loops has a common total duration.

18. The method of claim 17, wherein each of the MRI cine loops has a duration of at least one full cardiac cycle.

19. The method of claim 17, wherein frames for which the duration is adjusted are evenly distributed throughout the MRI cine loop.

20. The method of claim 1, wherein evaluation the compensated MRI cine loops comprise comparing at least two of the plurality of cine loops to each other.

21. The method of claim 20, wherein one of the at least two of the plurality of cine loops is a baseline MRI cine loop.

22. The method of claim 21, further comprising registering frames of the plurality of MRI cine loops to the baseline MRI cine loop.

23. A method according to claim 1, further comprising obtaining MRI images for the MRI cine loops using a fast gradient echo segmented k-space sequence having sufficient temporal resolution for identification of end of systole, the temporal resolution being between 13-65 ms, with lower times corresponding to faster heartbeats and higher times corresponding to slower heartbeats, and wherein the MRI cine loops are obtained using breathhold durations between 10-23 seconds, the longer breathhold durations associated with faster heartbeat rates.

24. The method of claim 23, wherein acquiring step is carried out using the k-space segmentation and breathhold durations for the specified differing heart rates according to:

| Heart Rate (beats/min) | Views per Segment | Temporal Resolution (msec) | Breathhold Duration (sec) |
| --- | --- | --- | --- |
| <55 | 10 | 65 | 10 |
| 55-65 | 8 | 52 | 13-11 |
| 65-95 | 6 | 39 | 15-10 |
| 95-125 | 4 | 26 | 15-12 |
| 125-170 | 2 | 13 | 23-17. |

25. A workstation according to claim 24, wherein the display is configured to accept user input to electronically select a plurality of dose amounts and a plurality of side-by-side anatomical views in response to clinician input whereby selected MRI cine loops are displayed responsive thereto, and wherein the display is configured to rapidly switch between various display mechanisms for evaluating the MRI cine loops of different doses of the stress-inducing substance at a same location of the heart and different locations of the same dose of the stress inducing substance.

26. The method of claim 1, further comprising electronically automatically comparing a baseline MRI cine loop of the patient to MRI cine loops at different heart rates.

27. The method of claim 26, further comprising electronically registering the differing MRI cine loops to the baseline loops such that corresponding pixels of the cine loops or portions of the cine loops are each associated with a same physical location within the patient.

28. A method of displaying MRI cine loops comprising:
adjusting a characteristic of one frame of a plurality of frames of an MRI cine loop with a processor,
wherein the MRI cine loops are generated using multiple MRI images that highlight thickening of the myocardia and form the frames of the cine loops,
wherein the characteristic is at least one of contrast, brightness, and gamma;
propagating the adjustment of the one frame to other frames of the MRI cine loop with the processor; and
adding frames to at least one of the plurality of MRI cine loops with the added frames evenly distributed through the at least one cine loop so that the cine loops represent different heart beats that are synchronized.

29. The method of claim 28, further comprising:
displaying a plurality of MRI cine loops during the adjusting step; and
automatically propagating the adjustment of the one frame of the MRI cine loop to frames of the other MRI cine loops.

30. The method of claim 28, wherein adjusting a characteristic comprises cropping a frame of the plurality of frames to provide a portion of the frame.

31. The method of claim 28, wherein adjusting a characteristic comprises adjusting a contrast, or brightness of a display level of the frame.

32. The method of claim 28, further comprising electronically storing the adjusted characteristic and subsequently displaying the MRI cine loops with the adjusted characteristic at a later time.

33. A cardiac diagnostic workstation, comprising:
a workstation with a display in communication with an MRI scanner;
a display processor in communication with the display configured to display a plurality of different views of temporally synchronized MRI cine loops of the heart of a patient in the MRI scanner in substantially real-time while the patient is in the MRI scanner, the MRI cine loops adjusted to have the same duration, the different views comprising some views associated with a first anatomical view of the heart of the patient at different heart rates induced by different doses of a stress-inducing substance and some views associated with different anatomical views of the heart of the patient at a substantially constant heart rate, wherein the MRI cine loops are generated using multiple MRI images that highlight thickening of the myocardia and form the frames of the cine loops,
wherein the display processor is configured to accept user input to electronically select at least one of the following: (a) one dose amount, (b) at least one anatomical view, and (c) at least one dose amount and at least one anatomical view, whereby selected MRI cine loops are displayed responsive thereto to allow a clinician to evaluate cardiac function and physiology during a stress test whereby the cine loops are displayed during the stress test to allow a physician to assess cardiac physiology of a patent so as to adjust parameters of the test and/or avoid injury to the patient thereby providing safer cardiac stress testing.

* * * * *

UNITED STATES PATENT AND TRADEMARK OFFICE
CERTIFICATE OF CORRECTION

PATENT NO. : 8,494,611 B2  
APPLICATION NO. : 10/629259  
DATED : July 23, 2013  
INVENTOR(S) : Hamilton et al.

Page 1 of 1

It is certified that error appears in the above-identified patent and that said Letters Patent is hereby corrected as shown below:

In the Claims:
Column 14, Claim 33, Line 21: Please correct "of a patent so as"
to read -- of a patient so as --

Signed and Sealed this
Twenty-second Day of April, 2014

Michelle K. Lee
*Deputy Director of the United States Patent and Trademark Office*